(12) United States Patent
Liebel et al.

(10) Patent No.: US 9,824,259 B2
(45) Date of Patent: Nov. 21, 2017

(54) DEVICE AND METHOD FOR MICROSCOPY ON A PLURALITY OF SAMPLES

(71) Applicants: KARLSRUHER INSTITUT FÜR TECHNOLOGIE (KIT), Karlsruhe (DE); ACQUIFER AG, Karlsruhe (DE)

(72) Inventors: Urban Liebel, Dielheim-Horrenberg (DE); Jochen Gehrig, Bretten (DE)

(73) Assignee: KARLSRUHER INSTITUT FUER TECHNOLOGIE (DE)

( * ) Notice: Subject to any disclaimer, the term of this patent is extended or adjusted under 35 U.S.C. 154(b) by 135 days.

(21) Appl. No.: 14/443,529

(22) PCT Filed: Oct. 29, 2013

(86) PCT No.: PCT/EP2013/003252
§ 371 (c)(1),
(2) Date: May 18, 2015

(87) PCT Pub. No.: WO2014/075764
PCT Pub. Date: May 22, 2014

(65) Prior Publication Data
US 2015/0317507 A1   Nov. 5, 2015

(30) Foreign Application Priority Data
Nov. 19, 2012   (DE) .................. 10 2012 022 603

(51) Int. Cl.
*H04N 7/18* (2006.01)
*G06K 9/00* (2006.01)
(Continued)

(52) U.S. Cl.
CPC ....... *G06K 9/00134* (2013.01); *G01N 21/253* (2013.01); *G02B 21/361* (2013.01);
(Continued)

(58) Field of Classification Search
None
See application file for complete search history.

(56) References Cited

U.S. PATENT DOCUMENTS

| 5,533,401 A | 7/1996 | Gilmore |
| 2004/0004759 A1 | 1/2004 | Olszak |

(Continued)

FOREIGN PATENT DOCUMENTS

| WO | 2006097123 | 9/2006 |
| WO | 2008028298 | 3/2008 |

OTHER PUBLICATIONS

BD Biosciences. BD Pathway Bioimaging Systems. San Jose: BD Biosciences, 2009. Print.
(Continued)

*Primary Examiner* — James M Anderson, II
(74) *Attorney, Agent, or Firm* — Onello & Mello, LLP

(57) ABSTRACT

The present invention relates to a device and a method for microscopy (100) of a plurality of samples (102), wherein the device comprises:—a first optical detector (106, 108), which is designed to consecutively adopt a plurality of measuring positions and to detect first image data (200) of a sample (104) with a first spatial resolution at each measuring position;—an image data analyser device which is designed to determine for each sample (202) a region (204) of the sample to be examined represented within the first image data (200) in each case;—a second optical detector (110, 112), which is coupled to the first optical detector (106, 108) in such a manner that the second optical detector (110, 112) tracks the first optical detector (106, 108) and therefore the second optical detector (110, 112) adopts measuring positions which the first optical detector (106, 108) had previously adopted. The second optical detector (110, 112) is designed to detect for each sample (202) respective second image data (300) from the region (204) to be examined in the sample (202) concerned, with a spatial resolution that is higher than the first spatial resolution.

10 Claims, 3 Drawing Sheets

Figure 1:
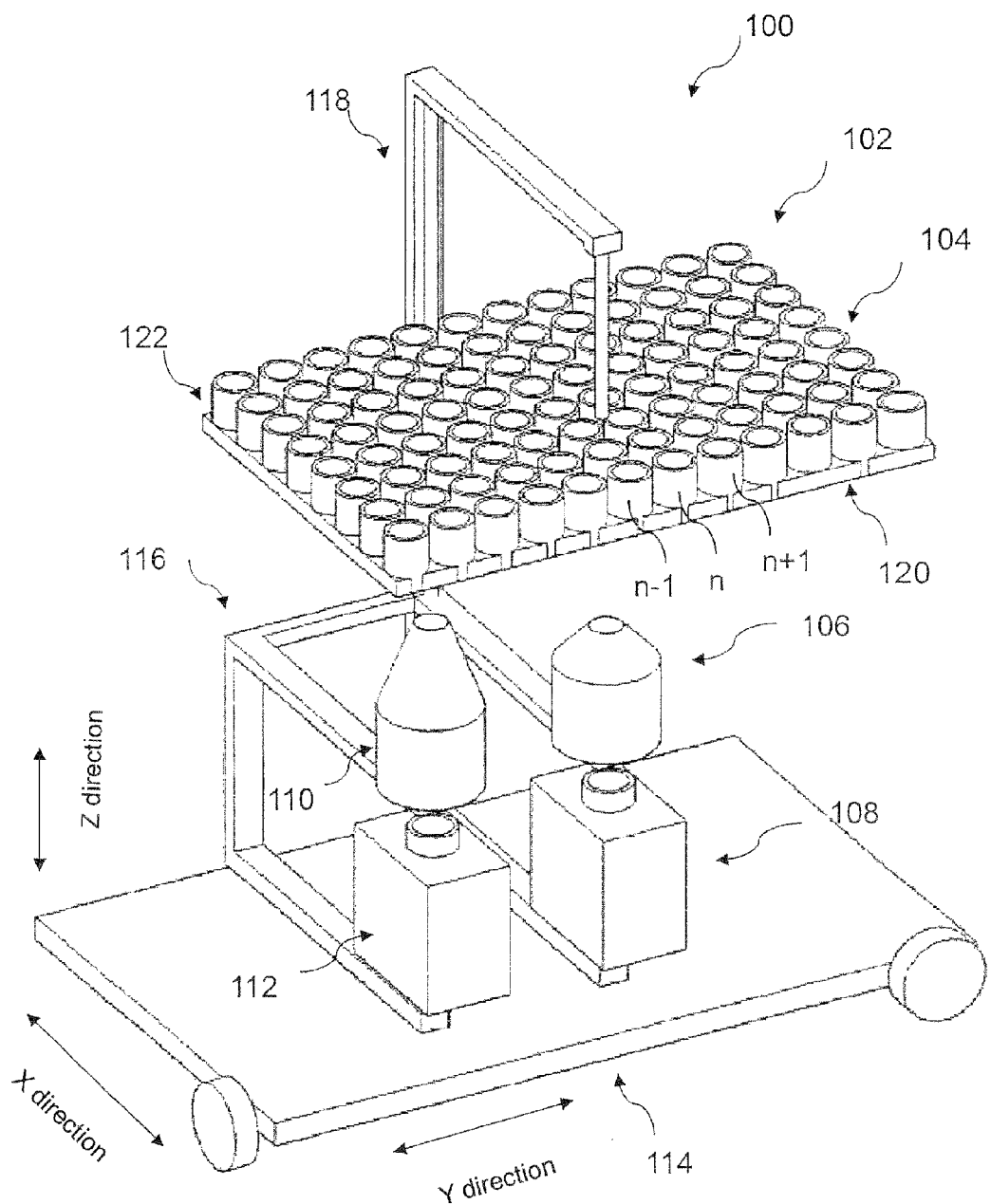

(51) Int. Cl.
    *G02B 21/36*     (2006.01)
    *G01N 21/25*     (2006.01)
    *G01N 35/00*     (2006.01)

(52) U.S. Cl.
    CPC ........... *G02B 21/367* (2013.01); *G01N 35/00* (2013.01); *G02B 21/362* (2013.01); *G06K 2209/403* (2013.01)

(56) References Cited

U.S. PATENT DOCUMENTS

| | | |
|---|---|---|
| 2008/0206774 A1 | 8/2008 | Tafas et al. |
| 2010/0103253 A1 | 4/2010 | Sieckmann et al. |
| 2010/0309306 A1 | 12/2010 | Uchiyama et al. |
| 2010/0310139 A1* | 12/2010 | Kimura .............. G02B 21/002 382/128 |
| 2012/0154773 A1 | 6/2012 | Beyer |

OTHER PUBLICATIONS

Pfriem, A. et al.: Robotersysteme fur Hochdurchsatzverfahren in der Bioanalysetechnik, at-Automatisierungstechnik, 59, 2011, pp. 134-140.
Peravali, R. et al.: Automated feature detection and imaging for high-resolution screening of zebrafish embryos BioTechniques 2011 pp. 319-324 vol. 50, No. 5.
International Search Report and Written Opinion dated Nov. 28, 2013 issued in International Application No. PCT/EP2013/003252.

\* cited by examiner

DEVICE AND METHOD FOR MICROSCOPY ON A PLURALITY OF SAMPLES

The present invention relates to a device for microscopy of a plurality of samples and a method for microscopy of a plurality of samples.

In a considerable portion of all microscopes used today, a sample needs to be moved in order to be able to examine it. A sample can be in particular a biological or non-biological material. A biological material can be in particular living or dead organisms. Furthermore, a biological material or respectively biological samples can be tissue, cell or fibre material, which is of human, animal or plant origin. Non-biological material can be for example a rock sample or a piece of metal.

Frequently, a sample is positioned under an objective of a microscope by means of automatic systems so that the sample can be examined. In particular, biological samples are frequently positioned in so-called microtiter plates. Microtiter plates are standard vessels for (in particular biological) samples. They usually have between approximately 12 and approximately 1536 wells/storage positions, in which cells, biological samples or another material are stored above all for optical examination. The microtiter plate is inserted or mounted into an automatic system. The automatic system is thereby designed such that the microtiter plate is displaceable/shiftable under or respectively in front of the objective so that each sample arranged in the microtiter plate can be positioned for an examination by means of the objective. Each sample in or respectively on a microtiter plate can thus be positioned consecutively for examination by means of the microscope until all samples or respectively storage positions have been examined or respectively photographed.

Such automatic systems or respectively automatic receiving devices typically allow the microtiter plate to be displaced in a 2-dimensional area. For example, a microtiter plate can be moved in a range of 120 mm×80 mm. In other words, a microtiter plate can be moved or displaced in a Cartesian work area. If the microtiter plate also has for example a size of 120 mm×80 mm, each region of the microtiter plate can be examined by means of the microscope or respectively be brought into the region of the optical axis of the objective of the microscope. In other words, the microtiter plate can be displaced in an X direction and/or a Y direction in order to examine a certain region of the microtiter plate or respectively a certain sample on the microtiter plate.

One important aspect in microscopy or respectively in the examination of samples is the detailed imaging of special structures or respectively regions of a sample. Different auto-focus systems can be used for this, which need a certain time before the picture or respectively photograph in order to bring the sample into the "correct" Z position (focussing). In other words, it is required for focussing that the distance between sample and objective is adjusted along the optical axis of the objective of the camera/microscope such that the structures to be examined are as clear as possible and easily identifiable.

Modern microscopes can identify "interesting structures" during focussing or shortly thereafter. It is hereby possible not only to focus the sample but also to shift or respectively position the sample so that the "interesting structure" of an image to be captured is moved or respectively positioned in the centre of the image if it would have otherwise been located in an edge area of a picture.

Many samples must be prepared for a microscopic examination. It is thereby often desirable that samples are examined already within a very short period after their preparation in order to minimize to the greatest extent possible undesired changes in the samples up until examination.

For example, it is important for living biological samples that an examination can be performed quickly since it is possible that the sample moves like a living organism within the storage position within the microtiter plate or even between individual storage positions within the microtiter plate and thus must always be "re-approached" so that a complete examination is possible because the image area of the microscope/camera is often smaller than the entire sample. Furthermore, it would be possible that a sample is only identifiable by its position in the microtiter plate. Accordingly, a sample that moves out of its position/storage position in the microtiter plate is hard to identify or is no longer identifiable. This problem is conceivable in particular when the individual samples are not arranged in a microtiter plate but rather in a petri dish or the like, in which the individual samples can move (freely).

Furthermore, only a certain small part of the sample is decisive for an examination so that it is not sufficient that any part of a sample is recorded/photographed. Rather, a special region/part of the sample must be examined in order to be able to collect valuable information or respectively knowledge.

It is also possible that a sample is only examinable at all for a limited period of time. In other words, it can happen that properties or respectively "uniquenesses" of a sample are only identifiable for a limited period of time. For example, after a certain period of time or respectively lifespan of the sample, certain reactions may no longer be examinable or respectively verifiable. The total number of samples to be examined that are positioned on a microtiter plate and examined consecutively is thus mainly dependent on the type of the sample and the type of the examination. However, the number of "examinable" samples on a microtiter plate is limited by these requirements, whereby the effort for examining a plurality of samples increases since a changing of microtiter plates and a readjustment of the microscope or respectively of the respective microtiter plate to the microscope is required more frequently.

If experiments are performed, in which the sample changes or respectively reacts with other substances, examinations of this sample should be performed as soon as possible. In order to be able to achieve scientifically reliable results, it is frequently necessary to perform the experiments on a plurality of samples in order to be able to examine comparative values with respect to their changes. Accordingly, it is necessary that the sample be examined in as timely a manner as possible after the addition of a substance etc. The same is applicable when a test series is to be performed and as many samples as possible need to be examined under the same prerequisites or respectively test conditions.

The object of the present invention is thus to provide a device and a method by means of which a plurality of samples can be examined consecutively as promptly as possible. In other words, one object is to provide a device and a method that enable the minimization of the time effort for the microscopic examination of a plurality of samples compared to known devices and methods.

According to the invention, this object is solved through the characteristics of the independent claims. Preferred embodiments of the invention are object of the dependent claims.

One aspect of the present invention relates to a device for microscopy of a plurality of samples, which are arranged in particular at a plurality of measuring positions. The device according to the invention comprises a first optical detector, which is designed to consecutively adopt a plurality of measuring positions in relation to a sample holder and to detect first image data of a sample (of the respective measuring position) with a first spatial resolution at each measuring position. For this, the device is designed in particular to move the first optical detector or respectively the sample holder such that the first optical detector adopts consecutively the plurality of measuring positions relative to the sample holder. For this, during the transfer from one measuring position to the next measuring position, the first optical detector moves relative to the sample holder or respectively the sample holder relative to the first optical detector. The first optical detector preferably remains mainly at rest during the capturing of the first image data relative to the sample holder, while a relative movement only takes place between the image capturing processes. In a particularly preferred embodiment, only the first optical detector, but not the sample holder, is accelerated and slowed again for the relative movement, while the sample holder remains at rest. The measuring process thereby influences the samples held by the sample holder as little as possible.

Particularly preferably, the device according to the invention has a control device, which sets the plurality of measuring positions preferably in a fixed or adjustably changeable, grid-like arrangement. A plurality of specifiable arrangements of the plurality of measuring positions is preferably stored in the control device. For example, each measuring position of the device (in particular of the first optical detector) can correspond to a sample vessel (e.g. well) in the microtiter plate. The arrangement of the measuring positions then corresponds to the arrangement of sample vessels in the microtiter plate. An arrangement (and preferably also a sequence) of measuring positions can thereby be stored (saved) for each of a plurality of standardized or conventional microtiter plates.

If then for example a user inserts a microtiter plate loaded with samples into the sample holder, he/she can select the corresponding specification for the arrangement and/or sequence of the measuring positions. The control device then preferably automatically controls the first optical detector such that it approaches consecutively the plurality of measuring positions (samples) according to the specified or respectively selected arrangement and/or sequence. Alternatively or in addition to a manual selection of a specified arrangement of measuring positions, the device can be designed to automatically identify and select the arrangement of measuring positions corresponding to a microtiter plate used.

Alternatively or in addition to the specification of fixed arrangements of measuring positions in the control unit, the device can also be designed for a free or a parameterized determination of the arrangement and/or sequence of the measuring positions. Thus, for example, a pattern of measuring positions in the form of a grid, in particular at regular or respectively the same distances from measuring positions (e.g. rectangular grid), can be specified, the grid dimension of which (e.g. distances between adjacent measuring positions along rows and/or columns) can preferably be freely specified by the user.

Moreover, the device according to the invention comprises an image data analyser device, which is designed to determine for each sample or measuring position (respectively) a region of the sample (the respective measuring position) to be examined represented within the respective first image data. This region to be examined is sometimes also referred to below as the "interesting" region of the sample. It thereby concerns in particular a section of the first image data, which needs to be examined more exactly (in particular enlarged and/or with a higher resolution and/or in its dynamics, i.e. time-resolved, and/or in a special optical spectral region). For example, the sample could be a cell culture, within which an individual cell or a cell group or a cell structure needs to be located and examined more closely. In tissue examinations, certain tissue structures could also be particularly interesting for the examination. In a preferred embodiment, the image data analyser device is designed to determine automatically (in particular through pattern recognition) the region of the sample to be examined.

The device according to the invention also comprises a second optical detector, which is coupled to the first optical detector in such a manner (directly or indirectly mechanically or through a corresponding activation) that it adopts consecutively a plurality of measuring positions, in particular the respective measuring positions, which the first optical detector had already adopted previously (directly or indirectly). In other words, the second optical detector tracks the first optical detector in its measuring positions. The second optical detector is thereby designed to capture for each sample second image data of the region of the respective sample or respectively of the respective measuring position to be examined with a second spatial resolution, which is higher than the first spatial resolution. The second optical detector thus tracks to a certain extent the first optical detector directly or indirectly and captures the second image data based on the data of the region to be examined determined by the image data analyser device (in particular an exact position within the first image data).

The device for microscopy can be in particular a microscope or respectively a microscope arrangement. In particular, the device is a device for serial or respectively sequential microscopy of a plurality of samples.

The first optical detector is preferably displaceable or respectively movable within a first detector working space (with respect to the sample holder or respectively the samples held thereby). For example, the first detector working space can be a 1-, 2- or 3-dimensional space. This first detector working space can be defined for example by means of a coordinate system so that a certain position of the first optical detector corresponds with a certain coordinate in the first detector working space. The coordinate system is preferably a Cartesian coordinate system, which enables the definition of a position of the first optical detector within the first detector working space through the specification of X and Y coordinates. In other words, the first optical detector is displaceable into an X and a Y direction, wherein the X and Y directions are preferably orthogonal to each other and fix an X-Y plane, which lies in particular perpendicular to an optical axis of the first optical detector.

If for example a plurality of samples is arranged in a matrix-like (grid-like) manner, these samples can be examined/examined by microscope by the first optical detector, in that the first optical detector approaches or respectively adopts sequentially different X-Y coordinates within the first detector working space, wherein each measuring position corresponds to an X-Y coordinate or a range of X-Y coordinates, and each measuring position is assigned to a respective sample or a sample vessel. In the direction of the optical axis of the first optical detector, the samples are preferably arranged at a distance from the first optical detector, which can be determined or respectively set in particular via a Z coordinate. If the first optical detector adopts a measuring position with respect to a sample, a measuring centre point of the sample preferably lies on or at least in the vicinity of the optical axis of the first optical detector. For example, a centre point of a storage position/well of a microtiter plate, in which a sample is arranged, can be defined/determined as the measuring centre point of the sample. In another embodiment, the plurality of samples is not arranged in a microtiter plate but rather in a Petri dish or the like. In this case, the Petri dish—for example by means of a (coordinate) grid—can be divided into subregions/cells, wherein each subregion/cell corresponds with a certain coordinate region. Each subregion/cell then corresponds to a measuring position of the first optical detector. The X-Y coordinate in the centre of the coordinate range of the cell can hereby be considered/defined as a measuring centre point of a sample.

A coordinate range of a measuring position $(X_1; Y_1)$ is preferably assignable to a coordinate range of a respective sample $(X_2; Y_2)$. The positions of the samples are preferably defined by means of a sample space. The sample space can be 1-, 2- or 3-dimensional. Furthermore, the sample space can be a Cartesian space, which is defined by orthogonal X, Y and Z axes. The samples are preferably arranged mainly in an X-Y plane, wherein each of the positions is defined or respectively determinable by coordinates. In other words, a position of a sample in the sample space can be expressed by a coordinate of the detector working space.

The samples and the first optical detector in a Z direction, which is arranged normally with respect to the X-Y plane, are preferably spaced from each other. The X-Y plane of the sample space is in particular parallel to the X-Y plane of the detector working space.

Correspondingly, a unique X-Y coordinate is assignable to each sample of the plurality of samples, which corresponds to a corresponding measuring position of the first optical detector.

It can be provided in particular that a sample is arranged at/on a certain position of a device for microscopy and remains there until completion of a microscopy/examination. In other words, it can be provided that a sample or respectively the plurality of samples is not moved during the microscopy/examination. In the case of a plurality of samples, a respective position/measuring position can be provided for each sample, at which the corresponding sample is arranged. For example, a plurality of samples can be positioned on one or more microtiter plates or the like, wherein this/these microtiter plate(s) can be arranged on/at a sample holder of the device for microscopy. The respective measuring position/coordinate of a sample is determined by the sample holder.

In a preferred exemplary embodiment, a sample holder can be shiftable or respectively displaceable so that a position of a sample at/on the device is changeable. It can preferably be provided that a position of a sample is only changed before or after a microscopy of a plurality of samples.

According to a further embodiment, the first optical detector can remain stationary during a microscopy, while the samples are positioned consecutively at the optical detector so that first image data can be captured. In this case, a measuring position is to be understood as a position or respectively sequential number of a sample, which allows a sample to be identified or respectively the image data to be assigned to a sample. For example, in a matrix-like arrangement of the plurality of samples, a specification of the row/column of a sample is considered its measuring position.

In particular, a first optical detector can comprise a photo and/or a video camera and/or a digital data processing. The first optical detector is designed in particular to capture first image data of a sample at each measuring position. First image data can comprise a picture or respectively photograph and/or a video recording. The first optical detector can comprise one or more objectives so that, depending on the sample, a corresponding objective can be selected, which should be used during a capturing of first image data. The objective and camera can preferably be used modularly. In other words, the objective is releasably connected with the camera so that the camera or respectively the objective is replaceable.

If for example a Petri dish or the like is used, which comprises a plurality of samples, the first image data of a sample comprise a representation according to the coordinate range or respectively the subrange/the cell, which is assigned to the sample.

In particular, a first spatial resolution is to be understood as a resolution power which allows that structures or respectively patterns of the respective samples are (sufficiently) detectable or respectively clearly defined. The first spatial resolution preferably has a resolution power so that the first image data can be evaluated or respectively analysed by the image data analyser device.

The image data analyser device can comprise in particular analysis software, which makes it possible to identify characteristics or respectively certain structures of a sample needing to be examined. The image data analyser device can preferably determine a range of a sample to be examined, for which first image data were captured, based on a structural comparison. The image data analyser device can preferably identify the colour schemes of samples and determine or respectively define a region of a sample to be examined based on them.

For example, a sample can have a certain basic pattern (basic structure). In this case, the image data analyser device can analyse/determine in which region of the first image data of the sample this basic pattern or respectively this basic structure is located. The region of the first image data, which contains this basic pattern or respectively this basic structure, can hereby be determined or respectively set as the region of the sample to be examined.

Furthermore, samples of a plurality of samples can have a certain basic pattern, wherein all samples in this basic pattern are similar or respectively the same. In this case, the image data analyser device can analyse/determine, in which region of the first image data of the respective samples this basic pattern or respectively this basic structure can be found so that the region of the first image data, which contains this basic pattern or respectively this basic structure, is determined or respectively set as the region to be examined for each sample of the plurality of samples.

The image data analyser device can preferably define or respectively identify a position or respectively a coordinate range, which corresponds to a position or respectively a coordinate range of the sample in the sample space or respectively detector working space, by analysing the first image data for the region to be examined.

The image data analyser device is preferably designed such that the image data analyser device can analyse various "interesting" structures. For example, the image data analyser device can comprise a user interface, by means of which structure data or respectively data on characteristics can be entered so that the image data analyser device analyses samples based on such an entry. In particular, the image data analyser device can analyse samples based on reference samples or respectively data. For example, the image data analyser device can access comparative image data of regions to be examined and, if similarities or respectively conformities are found in certain patterns/structures in a sample, this is determined as the region to be examined. For example, at least 70% of conforming patterns between comparative image data and a region of the sample can be defined as sufficient so that a region to be examined is determined/is determinable. The extent of the conformity can be, for example, variably adjustable and depend on the type of sample or respectively the type of examination.

The second optical detector can capture second image data of the sample based on a given region of the sample to be examined. The second optical detector preferably exclusively captures image data from the region of the sample to be examined.

The second image data preferably contain all "interesting" structures or respectively relevant elements of a sample so that an analysis of the sample can take place immediately and completely based on the second image data. The second optical detector can preferably be positioned "directly above" the region of a sample to be examined so that a centre point of the region to be examined lies on the optical axis of the second optical detector.

In particular, the second spatial resolution is higher than the first spatial resolution. The term "second spatial resolution" also means a resolution power of the second optical detector, which ensures that structures are clearly and distinctly identifiable. The second optical detector has a higher resolution power than the first optical detector so that a structure of a region of a sample to be examined can be examined more exactly than is possible with the first spatial resolution of the first optical detector. In particular, a resolution power of the second optical detector can be selected such that a comprehensive assessment or respectively analysis of the region to be examined can be performed. If, for example, tissue changes in nerve tissue are examined, then the second spatial resolution is selected such that all tissue structures are identifiable in a required clarity.

In particular, the second optical detector can comprise a photo camera and/or a video camera and/or digital data processing. The second optical detector can comprise one or more objectives so that a corresponding objective can be selected depending on the sample, which should be used during a capturing of second image data. The objective and camera (camera module) are preferably modularly usable. In other words, the objective is releasably connected with the camera (the camera module) so that the camera or respectively objective are replaceable.

The second optical detector is advantageously coupled with the first optical detector so that the second optical detector tracks the movements of the first optical detector. In other words, the first and the second optical detector are arranged "consecutively". Correspondingly, it is thus possible that the first optical detector captures or respectively detects first image data of a sample at a next measuring position, while the second optical detector captures second image data of a sample, for which the first optical detector has already captured first image data. The second optical detector tracks the first optical detector in its measuring positions so that the second optical detector adopts measuring positions, which the first optical detector had previously adopted.

In particular, the term "track" means that the second optical detector is moved from one measuring position to the next, wherein the first optical detector is also moved. The term "track" can also mean that the plurality of samples passes consecutively by the optical detectors. In this case, the samples would be moved and the optical detectors would remain stationary during a microscopy. In a further design, samples and detectors could be moved towards each other and past each other so that, after samples have been examined, the optical detectors and the subsequent samples are quickly positioned at the next measuring position. In other words, the samples and the optical detectors are moved.

The device for microscopy can be designed in particular so that it can be set whether the plurality of samples or the optical detectors or both, namely the optical detectors and the plurality of samples, should move during the microscopy in order to adopt respective measuring positions.

The second optical detector is preferably arranged in a measuring position "behind" the first optical detector. In other words, the second optical detector is located at the measuring position n, while the first optical detector is located at measuring position n+1. In another exemplary embodiment, the first and the second optical detector can be separated from each other by two, three or four measuring positions. The distance or respectively the number of measuring positions is preferably adjustable between the first and the second optical detector. Correspondingly, the first and the second optical detector can be coupled with each other mechanically. A coupling can preferably be infinitely variable/adjustable in order to set a distance between the first and second optical detector. According to one design, the first and the second optical detectors are permanently coupled to each other so that the distance between the optical detectors is mainly non-variable/changeable. In a further design, the detectors are coupled with each other such that the distance of the detectors with respect to each other is variably adjustable.

The first spatial resolution of the first optical detectors is preferably selected such that the first optical detector can capture first image data of an entire sample at a measuring position n+1, while a measuring centre point of the region of a sample to be examined lies at the measuring position n on the optical axis of the second optical detector. In other words, the first spatial resolution of the first optical detector is sufficient in order to capture a representation of a total sample/storage position by means of first image data, even if the measuring centre point of the sample/storage position does not lie on the optical axis of the first optical detector.

The time investment for the microscopy of a plurality of samples is advantageously reduced in that a sample is pre-examined by means of a first optical detector and, based on the results of this pre-examination, the second optical detector performs a main examination of a certain region to be examined. In particular, it is hereby advantageous that the second optical detector can immediately/directly move towards/approach and examine the region to be examined already based on exact information like position and size of an area to be examined, while the first optical detector already examines the next sample. In comparison, conventional auto-focus systems require that a sample first be examined completely, wherein a certain time is needed to identify the region to be examined and only then to move towards or respectively approach this region in order to perform further examinations.

Further preferably, the first optical detector and the second optical detector have parallel-spaced optical axes.

The optical axes of the first and of the second optical detector preferably have a gap, which corresponds with a distance Δd. The distance Δd can correspond for example with a distance between the centre point position of a measuring position/sample n and the centre point position of the next measuring position/sample n+1. Furthermore, the distance Δd can correspond with a distance between the centre point positions of a sample n and a sample n+2, a sample n and a sample n+3 or a sample n and a sample n+4. In other words, the first and the second optical detector can be separated from each other by two, three or four measuring positions.

In a preferred exemplary embodiment, the distance Δd is adjustable so that, depending on the requirement for an examination or respectively an experiment, the distance Δd of the optical axes of the first optical detector and of the second optical detector is adjustable.

Further preferably, the first optical detector and the second optical detector are coupled with each other via a detector holder. A parallel gap of the optical axis of the first optical detector to the optical axis of the second optical detector is preferably determined or respectively defined by means of the detector holder. A detector holder preferably comprises one or respectively more mechanical immobilizations, which enables a releasable coupling or respectively releasable connection of the first and of the second optical detector with the detector holder.

The detector holder advantageously enables that a parallel gap Δd of the optical axes of the first and of the second optical detector is adjustable. For example, a gap Δd can correspond to a distance between a centre point position of a measuring position/sample n and of the centre point position of the next measuring position/sample n+1. Furthermore, the distance Δd can correspond to a distance between the centre point positions of the sample n and of the sample n+2, of the sample n and the sample n+3 or of the sample n and the sample n+4. In other words, the first and the second optical detector can be separated from each other by two, three or four measuring positions, wherein this gap is adjustable by means of the detector holder.

The detector holder is preferably designed such that at least the second optical detector is displaceable relative to the first optical detector. In other words, the second optical detector, if mounted or respectively fixed on/at the detector holder, can adopt different positions during a microscopy. Correspondingly, the second optical detector is shiftable or respectively movable in one or two directions during a microscopy, wherein the first optical detector adopts a single/fixed position at/on the detector holder during a microscopy.

The first and the second optical detectors can advantageously be coupled with each other, wherein it is possible that the second optical detector can approach a measuring centre point of the region of a sample to be examined at the measuring position n, while the first optical detector approaches a measuring centre point of a sample at the measuring position n+1. However, due to the coupling of the first and of the second optical detector, it is only necessary to displace the second optical detector starting from a measuring centre point of a measuring position to a measuring centre point of a region to be examined.

Further preferably, the detector holder is coupled with a coordinate table so that the first and the second optical detector are shiftable relative to the plurality of samples.

The detector holder can be freely arrangeable on the coordinate table or connected at a fixed coupling area to the coordinate table. The detector holder is preferably releasably connectable with the coordinate table.

The first and the second optical detector can advantageously be coupled to each other in a simple manner by means of the detector holder, wherein the first and the second optical detector are controlled/regulated at the same time by a controlling/regulating of the coordinate table. In other words, the second optical detector is brought/displaced into the measuring position determined for it by approaching a measuring position with the first optical detector simultaneously/automatically. If the second optical detector is movable/displaceable relative to the first optical detector, the second optical detector can also be controllable/regulatable in order to adopt a certain position within its measuring position.

Further preferably, the first optical detector captures first image data based on a specified focussing, i.e. in the case of a focussing (distance adjustment) of an objective of the first optical detector on a specified object distance.

In other words, the first optical detector is designed such that a focussing of the first optical detector is sufficient in order to capture for each sample first image data, which make it possible to determine regions to be examined.

The term "specified focussing" means in particular that a focussing is adjustable for the first optical detector, wherein a certain focussing is preferably determined/specified or respectively set before a microscopy of a plurality of samples. This determined focussing is then preferably used during the entire microscopy. A suitable focussing can be selected or respectively set depending on the samples to be examined with a microscope.

The time span between the approach of a measuring position and the capturing of image data for an examination is hereby advantageously reduced since the first optical detector is in the position to capture first image data for a sample immediately after the adoption/approach of the measuring position. The second optical detector can—while the first optical detector captures first image data of a next sample—immediately capture second image data of a sample previously examined with a microscope since the second optical detector moves towards or respectively approaches immediately the determined region to be examined—of the sample previously examined with a microscope by the first optical detector—based on the data of the image analyser device.

A certain focussing has preferably also been determined or respectively set for the second optical detector before the start of a microscopy of a plurality of samples so that the focussing of the second optical detector does not need to be adjusted or only needs to be slightly adjusted when second image data are captured.

Further preferably, the first optical detector has a shorter focal width or respectively a lower magnification than the second optical detector. Further preferably, the first optical detector has a larger image field than the second optical detector. Further preferably, the first optical detector preferably has a higher depth of field than the second optical detector. Further preferably, the first optical detector has a lower image resolution than the second optical detector. Further preferably, the first optical detector has a shorter exposure time than the second optical detector.

In particular, an image field can be understood as the maximum size of a region of an object that can be captured by an optical detector when the object is focussed. In other words, an image field defines the maximum dimensions of an object or of a sample that are captured and rendered by image data. Furthermore, an image field can be understood as an image circle of an objective, wherein the image circle defines the area that an objective can represent. Furthermore, an image field can be understood as a format or respectively size of a film or respectively of an image sensor of a camera, on which a captured image/representation can be represented.

In particular, the depth of field can be understood as a measure for the enlargement of the sharp area in the object space of an imaging optical system. In other words, the depth of field is understood as the size of the distance area, within which an object/sample appears sufficiently sharply in the image of the camera optics.

The depth of field of the first optical detector is preferably selected such that all regions of a sample are represented sharply in the first image data. In other words, all regions of a sample, which have different distances to the objective of the first optical detector, are represented in a similarly sharp manner or respectively with sufficient sharpness. In other words, a focal plane with respect to the samples is set such that all/many regions of the sample lie to the greatest extent possible on or at least close to in front of or close to in back of the focal plane and are thus represented sharply in the first image data.

The depth of field of the second optical detector is preferably selected such that the regions to be examined of the plurality of samples are represented/rendered sharply in the captured second image data. In this case, an entire region to be examined can be represented similarly sharply. The depth of field of the second optical detector can continue to be set such that certain structures within a region to be examined are represented sharply on the second image data, while other structures for an examination or respectively analysis are shown less sharply or not sharply. A depth of field can be selected or respectively set for example based on a reference sample(s).

The depth of field of the first optical detector is preferably larger than the depth of field of the second optical detector. In the case of a fixed coupling of the two detectors, a focussing of the second optical detector can thus take place for example through a corresponding shifting of the second detector (or of its objective) along the optical axis without the simultaneous shifting of the first detector coupled to it causing the first image data (of the next measuring position) to become unsharp.

Analogously, the image field of the first detector is preferably large enough to permit, even in the case of a permanent coupling of the two detectors with each other, a (lateral) shifting of the second detector for alignment with the region to be examined within the first image data without the simultaneous (lateral) shifting of the first detector coupled to it causing the next sample to be pushed out of the image field of the first detector.

An image resolution can be understood in particular as the number of pixels or respectively image points and/or the noise performance of the image sensor of a camera. The image resolution of the first optical detector can be selected/set or respectively provided for example such that at least macrostructures are identifiable. In other words, it is preferably not required that the first optical detector captures all structures of a sample in detail. The image resolution is preferably sufficient that a region to be examined is clearly identifiable or definable based on the first image data.

The image resolution of the second optical detector is preferably set or respectively determined such that all structures or respectively all "interesting" structures within the region to be examined are clearly identifiable. The image resolution of the second optical detector is preferably selected such that the structures remain clearly visible in the case of a magnification of the second image data or respectively a zooming in on the second image data.

The focal width/magnification of the first optical detector preferably suffices to capture/create first image data, which represent structures of the samples sufficiently clearly so that a region to be examined can be determined. The magnification of the first optical detector is preferably selected such that a sample or respectively a storage position is completely contained or respectively comprised in the first image data.

In particular, the focal width/magnification of the first optical detector can be selected such that an image field or respectively image distance or respectively image angle is large enough to capture a sample or respectively a storage position comprehensively/completely. The magnification of the first optical detector can be selected or respectively determined depending on the samples to be examined/examined by microscope.

A comprehensive or respectively complete capturing of a sample can be understood in particular such that edge areas of samples are not captured by the first optical detector if the samples do not have "interesting" structures or regions to be examined in certain/all edge areas. Accordingly in such a case, a sample is only understood as a potentially "interesting" region or respectively an "interesting" structure. In other words, regions of samples that can be defined/determined/identified in advance as "uninteresting" or respectively as irrelevant can remain unconsidered during the capturing of first image data. In such a case, an image distance or respectively a magnification can be selected or respectively determined such that "uninteresting" regions are not captured by the first optical detector.

A focal width/magnification of the second optical detector is preferably selected such that a region to be examined is captured completely. In other words, the entire region to be examined is represented or respectively rendered by captured second image data. A size or respectively approximate size of regions to be examined of a plurality of samples is preferably estimable or respectively determinable depending on the samples to be examined by microscope. Accordingly, a focal width/magnification is preferably selected such that an "expected" or respectively "maximum" size of regions to be examined can be captured by means of the second optical detector, while the image distance or respectively the image angle suffices to represent the regions to be examined completely. Further preferably, a magnification is selected such that "interesting" structures or respectively aspects to be examined of a region to be examined are captured or respectively represented in an enlarged manner such that an analysis is enabled.

The first optical detector can have for example one or more zoom objectives and/or replaceable objectives. The second optical detector can also have for example one or more zoom objectives and/or replaceable objectives. A suitable objective of the first and/or of the second optical detector can preferably be selected based on a reference sample(s). In this case, one or more of the samples to be examined by microscope or comparable or respectively similar samples can be used to determine a suitable magnification/image field/depth of field or respectively to find/select a suitable objective. This selection can preferably be performed automatically. Alternatively or additionally, objectives can be selected based on sample specifications or respectively sample properties. This selection can preferably take place based on database queries and/or in a computer-aided manner by means of user entries.

The results of such a selection process can be transmitted to the device for microscopy preferably directly or by means of a data transfer so that a suitable objective is used automatically.

The speed for a microscopy of a plurality of samples can advantageously be reduced through the use of the first and the second optical detector, wherein, at the same time, the costs for the provision of two optical detectors only increase slightly since only the second optical detector must meet particularly high standards with respect to the image quality, as is common for laboratory microscopes.

Further preferably, the first optical detector and the second optical detector preferably have a common focal plane.

Further preferably, the first optical detector comprises a webcam. Further preferably, the first optical detector comprises a CCD sensor. Further preferably, the first optical detector comprises a CMOS sensor. Further preferably, the first optical detector comprises a fluorescence detector. Further preferably, the second optical detector comprises a CCD sensor. Further preferably, the second optical detector comprises a CMOS sensor. Further preferably, the second optical detector comprises a fluorescence detector.

In particular, a webcam can be understood as a recording device or respectively camera, which can transmit captured first image data to an image analyser device by means of a data transfer cable or respectively a data transfer interface. Furthermore, a webcam can be understood in particular as a camera, which can take pictures at (short) intervals.

Further preferably, the device comprises a manipulation device for manipulating samples.

In particular, a sample can be influenced by means of the manipulation device. For example, a manipulation device can comprise a dispenser for one or more substances so that samples can react with a substance shortly before or during the capturing of image data. This is particularly advantageous when a reaction between a sample and a substance takes place very quickly in terms of time. In this case, the entire period of the reaction can be easily captured.

Furthermore, the manipulation device can comprise or respectively carry tools or respectively examination equipment so that for example mechanical actions can be taken on a sample before or during an examination of the sample. A manipulation device is preferably arranged such that samples can be manipulated before or during a capturing of first and/or second image data. The manipulation device is preferably designed such that examination equipment can be changed or respectively replaced.

For example, a needle or respectively cannula could be examination equipment of the manipulation device. Furthermore, a device for microscopy can comprise two or more manipulation devices. The manipulation devices are preferably connected/coupled with the device in a releasably coupleable/connectable manner. Furthermore, the manipulation devices can be shiftable or respectively moveably coupled or respectively mounted. Alternatively or additionally, the manipulation devices can be coupled/coupleable with the device at specified coupling areas.

One or more manipulation devices can preferably be arranged or respectively coupled to the detector holder.

Further preferably, another optical detector can be coupled to the manipulation device.

Further preferably, for capturing second image data, the second optical detector adopts a position, in which a centre of a region to be examined lies on the optical axis of the second optical detector.

In other words, the second optical detector approaches the region to be examined, if applicable, so that the region to be examined is positioned in the best possible manner in the image centre of the second image data.

According to one design, the first and the second optical detectors are coupled to each other such that a movement/displacement of the second optical detector equally leads to a displacement of the first optical detector. In this case, the image field of the first optical detector is selected to be large such that it is ensured that the first optical detector captures first image data of a "complete" or respectively "total" sample. In other words, the image field of the first optical detector is adjusted so that the first image data of the first optical detector always contains the sample or respectively the relevant regions of a sample.

In another embodiment, the second optical detector is relatively movable/shiftable with respect to the first optical detector so that the second optical detector is movable or respectively shiftable in certain limits or respectively a certain coordinate range regardless of a movement of the first optical detector.

Another aspect of the present invention relates to a method for microscopy of a plurality of samples, which are arranged in particular at a plurality of measuring positions, comprising:

detection of first image data by means of a first optical detector, which is designed to consecutively adopt a plurality of measuring positions and to detect first image data of a sample, which is assigned in particular to a respective measuring position, with a first spatial resolution at each measuring position;

identification (determination) of a region to be examined by means of an image data analyser device, which is designed to determine for each sample or respectively measuring position a region of the sample to be examined (assigned to this measuring position) represented within the first image data in each case; and detection of second image data by means of a second optical detector, which is coupled to the first optical detector in such a manner that the second optical detector tracks the first optical detector so that the second optical detector adopts (consecutively) measuring positions which the first optical detector had previously adopted and wherein the second optical detector is designed to detect for each sample or respectively measuring position second image data from the region to be examined in the sample concerned (assigned to this measuring position) with a second spatial resolution that is higher than the first spatial resolution.

The captured second image data are preferably assessed or respectively analysed, wherein this can occur in a computer-aided or respectively fully automated manner. Alternatively or additionally, an analysis of second image data can be performed by a user.

The method for the microscopy of a plurality of samples can preferably comprise one or more aspects with respect to the use or respectively design of the device for microscopy.

Figure 2:
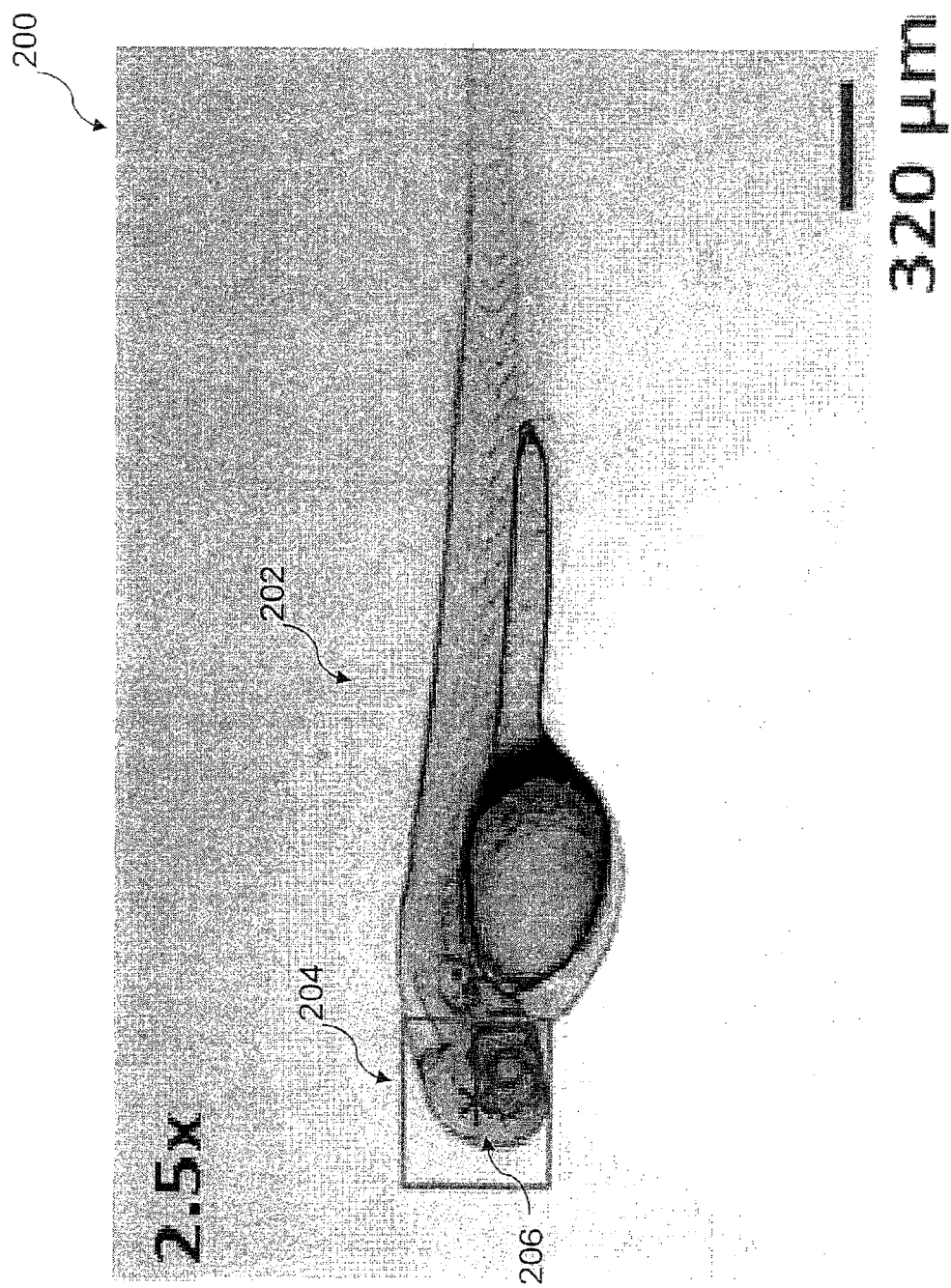

The invention is described as an example below based on accompanying drawings. The drawings show:

FIG. 1: a schematic representation of a device for microscopy;

FIG. 2: a representation of first image data and

Figure 3:
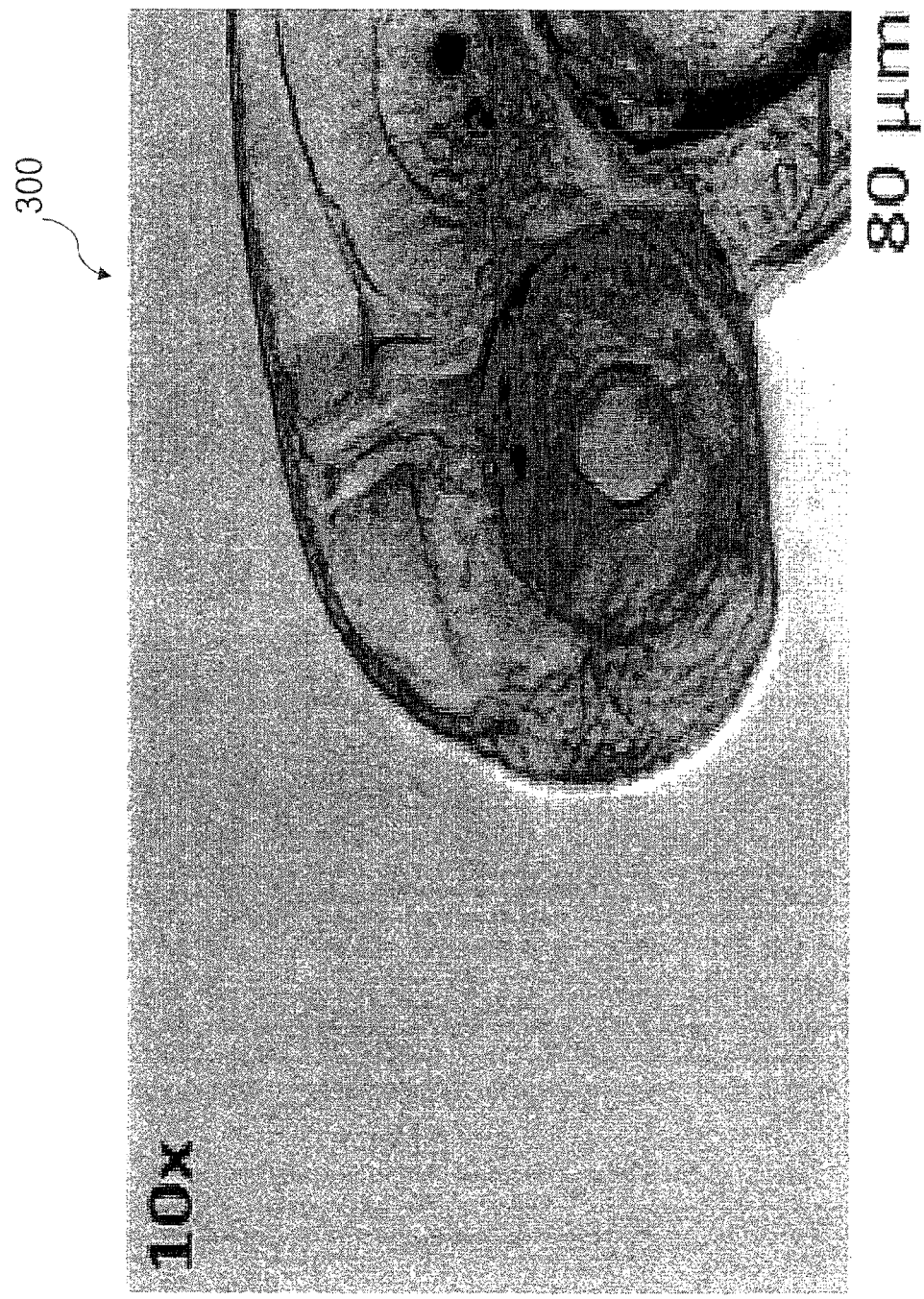

FIG. 3: a representation of second image data.

FIG. 1 shows a schematic representation of a device for microscopy 100, which comprises a first optical detector 106, 108 and a second optical detector 110, 112. The first optical detector comprises in particular a first objective 106 and a first camera module 108. The second optical detector comprises a second objective 110 and a second camera module 112. The first optical detector 106, 108 and the second optical detector 110, 112 are coupled together by means of a detector holder 116. The detector holder 116 is arranged on a coordinate table 114. The coordinate table 114 can be for example a motorized XY stage. Accordingly, the two detectors can be shifted or respectively moved by shifting or respectively moving the detector holder 116. In particular, the optical detectors can thus be moved synchronously relative to a sample holder 120. The device 100 also comprises a manipulation device 118, with which samples can be acted on chemically and/or mechanically. For example, substances can be added to the samples.

As can be seen in FIG. 1, a plurality of samples 102 can be positioned in a matrix-like manner on the sample holder 120 of the device 100. Each sample 104 is hereby arranged in a storage vessel 122. The storage vessels are thereby arranged in rows and columns in particular in a grid-like or respectively matrix-like manner preferably with the same distances.

The plurality of samples 102 can be examined/examined by microscope by the first optical detector 106, 108 in that the first optical detector 106, 108 approaches or respectively adopts consecutively different X-Y coordinates within the first detector working space, wherein each measuring position corresponds with an X-Y coordinate, and each measuring position is assigned to a respective sample 104 or respectively a corresponding storage vessel. For this, a predetermined definition (determination) of the grid, i.e. of the position of the individual measuring positions, is preferably saved in the device 100. The samples 104 are arranged spaced from the first optical detector 106, 108 in a Z direction, i.e. in particular in a direction parallel to an optical axis of the first objective 106. Once the first optical detector 106, 108 has adopted a measuring position with respect to a sample 104, a measuring centre point of a sample 104 preferably lies on or at least near the optical axis of the first optical detector 106, 108. For example, a centre point of a storage vessel 122, in which a sample 104 is arranged, can be defined/determined as the measuring centre point of the sample 104.

In another embodiment, the plurality of samples 102 is not arranged in a microtiter plate or in storage vessels 122, but rather in a Petri dish or the like. In this case, the Petri dish can be divided into subregions/cells, for example by means of a (coordinate) grid, wherein each subregion/cell corresponds with a certain coordinate region. Each subregion/cell then corresponds with a measuring position of the first optical detector. The X-Y coordinate in the centre of the coordinate region of the cell can hereby be considered/defined as the measuring centre point of a sample.

The second optical detector can be arranged at a measuring position "behind" the first optical detector. In other words, the second optical detector is located at the measuring position n, while the first optical detector is located at the measuring position n+1. In another exemplary embodiment, the first and the second optical detector can be separated from each other by two, three or four measuring positions. The distance or respectively the number of measuring positions is preferably adjustable between the first and the second optical detector. Correspondingly, the detector holder 116 is adjustable so that a coupling is infinitely adjustable/variable in order to set a distance between the first and the second optical detector, in particular between an optical axis of the first objective 106 and an optical axis of the second objective 110.

The first optical detector 106, 108 can be understood in particular as a pre-detector, with which preliminary examinations of samples are performed. The second optical detector 110, 112 can be understood in particular as a main detector, with which detailed examinations of samples are performed. Through the pre-detector 106, 108 (camera 108), which is attached offset with respect to the main detector 110, 112, structures can already be identified and analysed at an (n+1) position (next sample), which already provide/ "feed" information on a position in particular in an X,Y plane and/or colour of sample structures to the main detector 110, 112, while the main detector 110, 112 examines a sample at the position n. The information for the main detector 110, 112 are captured in particular by means of an image analyser device (not shown), which transmits corresponding data to the main detector 110, 112. The special structure of the microscope 100 according to the invention permits the positioning of an offset camera 108 outside the optical path of the main detector 110, 112. The main detector 110, 112 thereby wastes no time on detecting structures, but rather moves directly to the corresponding position provided by the pre-detector 106, 108.

Pre-detector 106, 108 and main detector 110, 112 preferably communicate with each other by means of a computer or a communication interface, which delivers from the first image data of the pre-detector 106, 108 to the main detector 110, 112 information in particular on the position and/or colour and/or structure. Both pre-detector 106, 108 as well as main detector 110, 112 preferably contain an application-specific optical system and a CCD- and/or CMOS-based sensor. It can preferably be provided by default that the main detector 110, 112 in a standard configuration has a so-called standard "wide-field" structure with fluorescence detection capability. This can also apply to the pre-detector 106, 108, wherein it—depending on the use—can comprise a simple webcam, which has a "fixed" magnification.

The ratio of magnification of the pre-detector at a position/measuring position n to the main detector is variable and depends on the use; i.e. it depends on the type of pre-detection that is performed. Particularly preferably, the pre-detection is performed with little magnification. The pre-detector at position n can preferably detect a large region with high depth of field with simultaneously low resolution. The (first) image data from the pre-detection are processed in real time with the help of image processing software (e.g. Labview, Matlab or open source packets). The goal of this automatic image processing is the automatic detection of a structure or region of interest and the extraction of the corresponding X,Y parameters/coordinates. These coordinates/parameters are used to centre the main detection objective below the detected region/area to be examined and to capture corresponding high-resolution 2-dimensional or respectively 3-dimensional representations/data as second image data.

FIG. 2 shows first image data 200 of a sample 202, which were captured, for example, with a first detector 106, 108. The sample shown here in FIG. 2 is a zebrafish larva. The first image data 200 were created with a first magnification, which is identified in FIG. 2 with the designation "2.5x". However, for further examination/main examination, only the brain of the zebrafish larva is interesting/relevant so that image data of the other regions of the zebrafish larva are not required. However, since the position of the brain within a sample vessel is not known in advance, it would take a comparatively long time to find the actual position of the brain in the case of an initial focussing on an image size which corresponds to the size of the brain. However, based on the overview in the first image data, the exact position of the brain can be easily determined. Upon specification of certain image structures, this can even preferably take place automatically.

For this, the first image data 200 are analysed or respectively assessed by an image analyser device (not shown), wherein the image analyser device only determines the "interesting" region of the sample, namely the brain of the zebrafish larva, as the region to be examined. The region to be examined determined by the image analyser device is shown framed in a box 204 in FIG. 2. The position of the box 204 in the first image data can be converted or respectively transformed into a position or respectively a coordinate range, which this region 204 of the sample has in the storage vessel (sample vessel). In other words, it can be determined based on first image data 200, which position/coordinates the second optical detector 110, 112 must adopt in order to be able to capture second image data of the sample from this region 204 or respectively in which coordinate range second image data of the sample must be captured. A marking 206 within the region 204 to be examined marks a centre point of the region to be examined based on which a position/measuring position of the second optical detector 110, 112 can be approached or respectively moved towards.

The first spatial resolution of the first optical detector 106, 108 is preferably selected such that the first optical detector 106, 108 can capture the first image data 200 of an entire sample 104 at a measuring position n+1, while a measuring centre point of the region to be examined of another sample 104 lies at the measuring position n on the optical axis of the second optical detector 110, 112. In other words, the first spatial resolution or respectively an image area of the first optical detector 106, 108 suffices to capture a representation of an entire sample 104 or respectively storage position by means of first image data 200, even if the measuring centre point of the sample/storage position does not lie on the optical axis of the first optical detector 106, 108. This can be the case for example when the second optical detector 110, 112 approaches a centre point 206 of a region 204 to be examined, which lies outside of a measuring centre point of the (previously examined or respectively to be examined) sample for the first optical detector, wherein however the first and the second optical detector are preferably permanently coupled to each other so that a movement of the one detector leads directly to the same movement of the other detector.

FIG. 3 shows second image data 300, which represent a determined region 204 of the zebrafish larva/sample 202 to be examined from FIG. 2 with a second magnification, which is identified in FIG. 3 with the designation "10x". As can be seen in FIG. 3, the second image data 300 comprise a representation of a section of the zebrafish larva, which includes the total determined region to be examined.

In the preferred embodiment shown in FIG. 3, the magnification and/or the resolution of the second image data 300 is approximately 4 times greater than the magnification or respectively resolution of the first image data 200 in FIG. 2. In general, the magnification and/or the resolution of the second optical detector is greater in the range of approximately 1 to approximately 1000 times, further preferably in the range of approximately 1 to approximately 100 times than the magnification and/or the resolution of the first detector. In another aspect, the magnification and/or the resolution of the second optical detector is preferably at least approximately 2 times, even more preferably at least approximately 4 times greater than the magnification and/or the resolution of the first optical detector. In particular, a magnification range or respectively a ratio of the magnification of the first optical detector to that of the second optical detector can be determined or respectively selected depending on the use. The magnifications of the optical detectors can preferably be set or respectively determined before a microscopy.

As can be seen in FIGS. 2 and 3, the first optical detector 106, 108 takes a low-resolution image (first image data 200) at a measuring position n−1. According to this example, this takes place with an objective which magnifies for example approximately 2.5 times. The image analyser device detects the embryonal head region, which was determined/defined as an "interesting" structure or respectively the region 204 to be examined, preferably automatically, in particular based on an automatic pattern identification. Second image data 300 of a sample 202, which are high-resolution and taken for example with a 10× magnifying objective, are then captured by means of the second optical detector 110, 112 at the measuring position n−1 for the region 204 to be examined. While the second optical detector 110, 112 captures the second image data 300 at the measuring position n−1, the first optical detector is already at the measuring position n and captures (new) first image data for another sample.

The images in FIGS. 2 and 3 are similar to the pictures in Peravali, R., Gehrig, J., et al. Biotechniques 50(5): 319-324. With the present invention, as described above based on a preferred embodiment referencing these figures, such images can be generated and analysed substantially more efficiently for a plurality of samples.

LIST OF REFERENCE NUMBERS

100 Device for microscopy
102 Plurality of samples
104 Sample
106 Objective of the first optical detector (first objective)
108 Camera module of the first optical detector
110 Objective of the second optical detector (second objective)
112 Camera module of the second optical detector
114 Coordinate table
116 Detector holder
118 Manipulation device
120 Sample holder
122 Storage vessel
200 First image data 200
204 Region to be examined
206 Marking, centre point of the region to be examined
300 Second image data

The invention claimed is:

1. A device for microscopy of a plurality of samples, comprising:
    a first optical detector, which is configured to consecutively adopt a plurality of measuring positions and to detect first image data of a sample with a first spatial resolution at each measuring position;
    an image data analyser device which is configured to determine for each sample a region of the sample to be examined represented within the respective first image data;
    a second optical detector, which is coupled to the first optical detector in such a manner that adopts consecutively a plurality of measuring positions, which the first optical detector had previously adopted and wherein the second optical detector is configured to capture for each sample second image data from the region to be examined of the respective sample with a second spatial resolution, which is higher than the first spatial resolution.

2. The device according to claim 1, wherein the first optical detector and the second optical detector are coupled with each other via a detector holder such that an optical axis of the first optical detector and an optical axis of the second optical detector are arranged parallel to each other at set distance.

3. The device according to claim 2, wherein the detector holder is coupled with a coordinate table so that the first and the second optical detector are shiftable relative to the plurality of measuring positions.

4. The device according to claim 1, wherein the first optical detector captures the first image data based on a specified focusing.

5. The device according to claim 1, wherein the first optical detector has a shorter focal width and/or a larger image field and/or a higher depth of field and/or a lower image resolution and/or a lower exposure time than the second optical detector.

6. The device according to claim 1, wherein the first optical detector and the second optical detector have a common focal plane.

7. The device according to claim 1, wherein the first optical detector comprises a webcam and/or a CCD sensor and/or a CMOS sensor and/or fluorescence detector, and wherein the second optical detector comprises a CCD sensor and/or a CMOS sensor and/or a fluorescence detector.

8. The device according to claim 1, wherein the device comprises a manipulation device for manipulating samples.

9. The device according to claim 1, wherein the second optical detector adopts a position for capturing second image data, in which a centre of a region to be examined lies on an optical axis of the second optical detector.

10. A method for microscopy of a plurality of samples, comprising:
detecting first image data with a first optical detector, which is configured to consecutively adopt a plurality of measuring positions and to detect first image data of a sample with a first spatial resolution at each measuring position;
determining a region to be examined with an image data analyser device, which is configured to determine for each sample a region of the sample to be examined represented within the respective first image data; and
detecting second image data with a second optical detector, which is coupled to the first optical detector in such a manner that the second optical detector tracks the first optical detector so that the second optical detector adopts measuring positions which the first optical detector had previously adopted and wherein the second optical detector is configured to detect for each sample second image data from the region to be examined in the respective sample with a second spatial resolution that is higher than the first spatial resolution.

* * * * *